United States Patent
Brodsky

(10) Patent No.: US 7,917,309 B2
(45) Date of Patent: Mar. 29, 2011

(54) SYSTEM AND METHOD FOR DETECTION AND PREVENTION OF INFLUX OF AIRBORNE CONTAMINANTS

(75) Inventor: Colin Brodsky, Salt Point, NY (US)

(73) Assignee: International Business Machines Corporation, Armonk, NY (US)

( * ) Notice: Subject to any disclaimer, the term of this patent is extended or adjusted under 35 U.S.C. 154(b) by 264 days.

(21) Appl. No.: 11/954,127

(22) Filed: Dec. 11, 2007

(65) Prior Publication Data

US 2009/0150090 A1    Jun. 11, 2009

(51) Int. Cl.
*G01N 31/00* (2006.01)
*B60H 1/00* (2006.01)

(52) U.S. Cl. .................. 702/31; 454/75; 454/239

(58) Field of Classification Search .............. 702/30–32, 702/45, 80, 182; 454/75, 103–105, 107–109; 700/266, 275–276; 701/22, 36, 45
See application file for complete search history.

(56) References Cited

U.S. PATENT DOCUMENTS

| | | | |
|---|---|---|---|
| 5,132,663 A * | 7/1992 | Strobl et al. ............... 340/438 |
| 5,571,401 A | 11/1996 | Lewis et al. | |
| 6,206,775 B1 | 3/2001 | Lemaitre et al. | |
| 6,495,892 B2 | 12/2002 | Goodman et al. | |
| 6,711,470 B1 | 3/2004 | Hartenstein et al. | |
| 6,792,339 B2 | 9/2004 | Basson et al. | |
| 6,899,081 B2 * | 5/2005 | Bielicki et al. ............... 123/402 |
| 7,144,553 B2 | 12/2006 | Lewis et al. | |
| RE40,767 E * | 6/2009 | Peterson et al. ............ 250/338.5 |
| 2007/0243808 A1 * | 10/2007 | Mathur et al. ................ 454/75 |
| 2008/0154671 A1 * | 6/2008 | Delk ................................. 705/7 |
| 2009/0018780 A1 * | 1/2009 | Sookhu ............................ 702/24 |

OTHER PUBLICATIONS

M.A. Ryan, H. Zhou, Automotive and Aerospace Application, Chapter 27, pp. 525-546, (2004), from the Handbook of Machine Olfaction: Electronic Nose Technology. http://www.le.ac.uk/eg/tcp1/book/content.htm.

* cited by examiner

*Primary Examiner* — Andrew Schechter
*Assistant Examiner* — Mary C O'Malley
(74) *Attorney, Agent, or Firm* — Wenjie Li

(57) ABSTRACT

An apparatus and method for detection of airborne contaminants and prevention of influx of the contaminants into an enclosed space, such as a vehicle cabin. A first sensor array samples exterior air prior to influx of the exterior air into the enclosed space. The first sensor array generates data uniquely corresponding to each contaminant. Data corresponding to predetermined contaminants is stored in computer memory. A user may also cause data corresponding to a contaminant selected by the user to be stored in the computer memory. Upon identification of a contaminant, an actuator is operative to control a position of a valve to prevent influx of the exterior air into the enclosed space.

14 Claims, 3 Drawing Sheets

SYSTEM AND METHOD FOR DETECTION AND PREVENTION OF INFLUX OF AIRBORNE CONTAMINANTS

BACKGROUND OF THE INVENTION

The invention relates generally to control of heating, ventilation, and air conditioning (HVAC) systems. More particularly, the invention relates to a system for detecting airborne contaminants and preventing influx of such contaminants into an enclosed space, such as a vehicle passenger compartment, via a HVAC system.

U.S. Pat. No. 6,206,775 (Lemaitre et al., "the '775 patent") discloses a motor vehicle heating or air conditioning apparatus including a sensor for detecting a pollutant such as carbon monoxide. Upon detection of a pollutant in the air supplied to the passenger compartment, position of an air intake flap is controlled to modulate flow of exterior air into the passenger compartment. The '775 patent discloses the sensor being adapted to identify relative concentrations of specific pollutants, such as carbon monoxide, using a comparator suitable for comparing a signal associated with a measured pollutant concentration with a reference signal associated with a threshold concentration, below which a level of the pollutant is acceptable (see column 3, line 53 to column 4, line 13). The '775 patent thus discloses a system including a sensor which is capable of identifying a limited set of one or more pre-defined pollutants.

U.S. Pat. No. 6,495,892 (Goodman et al., "the '892 patent") discloses a system for detecting and identifying analytes in a fluid. In particular, the '892 patent discloses a sensor array formed on an integrated circuit capable of generating an electrical signal which is a "fingerprint" of a given analyte. Pattern recognition processing may be used to identify the analytes on the basis of the "fingerprint" patterns (see column 9, lines 28-43). The '892 patent discloses that the sensor array may be formed from a plurality of sensors formed from conducting polymers the electrical properties of which change when the polymers are exposed to a given analyte, The '892 patent discloses a sensor array which is pre-programmed with a finite set of fingerprint patterns associated with a finite set of pre-defined analytes.

U.S. Pat. No. 5,571,401 (Lewis et al.) discloses a sensor array, of a type similar to that disclosed by the '892 patent, which is capable of distinguishing between first and second concentrations of a given chemical analyte based on measured resistance differences across chemically sensitive resistors (see the Abstract).

A need exists for an apparatus and method of detection and avoidance of airborne contaminants, the operation of which is not limited to a set of pre-defined contaminants.

BRIEF SUMMARY OF THE INVENTION

Briefly stated, in a first aspect the invention is a system for detection of airborne contaminants and prevention of influx of the contaminants into a vehicle cabin. The vehicle cabin is provided with a ventilation system including at least one valve. The system comprises a first sensor array adapted to sample exterior air prior to influx of the exterior air into the cabin. The first sensor array is capable of generating data uniquely corresponding to each contaminant. A microprocessor is operably coupled to the first sensor array. A computer memory is operably coupled to the microprocessor and has data stored therein corresponding to one or more predetermined contaminants. Input means are provided wherein a user can cause data corresponding to a contaminant selected by the user to be stored in the computer memory. An actuator is operably coupled to the microprocessor. The first sensor array generates data for comparison with data stored in the computer memory to identify contaminants in the exterior air. The actuator is operative to control a position of the at least one valve to prevent influx of the exterior air into the cabin upon identification of a contaminant having data stored in the computer memory.

In a second aspect, the invention is a method for detection of airborne contaminants and prevention of influx of the contaminants into a vehicle cabin. The vehicle cabin is provided with a ventilation system including at least one valve. The method comprises a step of providing a first sensor array adapted to sample exterior air prior to influx of the exterior air into the cabin. The first sensor array is capable of generating data uniquely corresponding to each contaminant. In another step, a microprocessor operably coupled to the first sensor array is provided. A computer memory operably coupled to the microprocessor and having data stored therein corresponding to one or more predetermined contaminants is provided. Input means wherein a user can cause data corresponding to a contaminant selected by the user to be stored in the computer memory is provided. The first sensor array is used to generate data for comparison with data stored in the computer memory to identify contaminants in the exterior air. Upon identification of a contaminant having data stored in the computer memory, an actuator operably coupled to the microprocessor is used to control a position of the at least one valve to prevent influx of exterior air into the cabin.

In a third aspect, the invention is a system for detection of airborne contaminants and prevention of influx of the contaminants into an enclosed space. The enclosed space is provided with a ventilation system including at least one valve. The system comprises a first sensor array adapted to sample exterior air prior to influx of the exterior air into the enclosed space. The first sensor array is capable of generating data uniquely corresponding to each contaminant. A microprocessor is operably coupled to the first sensor array. A computer memory is operably coupled to the microprocessor and has data stored therein corresponding to one or more predetermined contaminants. Input means are provided wherein a user can cause data corresponding to a contaminant selected by the user to be stored in the computer memory. An actuator is operably coupled to the microprocessor. The first sensor array generates data for comparison with data stored in the computer memory to identify contaminants in the exterior air. Upon identification of a contaminant having data stored in the computer memory, the actuator is operative to control a position of the at least one valve to prevent influx of the exterior air into the enclosed space.

BRIEF DESCRIPTION OF THE SEVERAL VIEWS OF THE DRAWINGS

The following detailed description of preferred embodiments of the invention will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
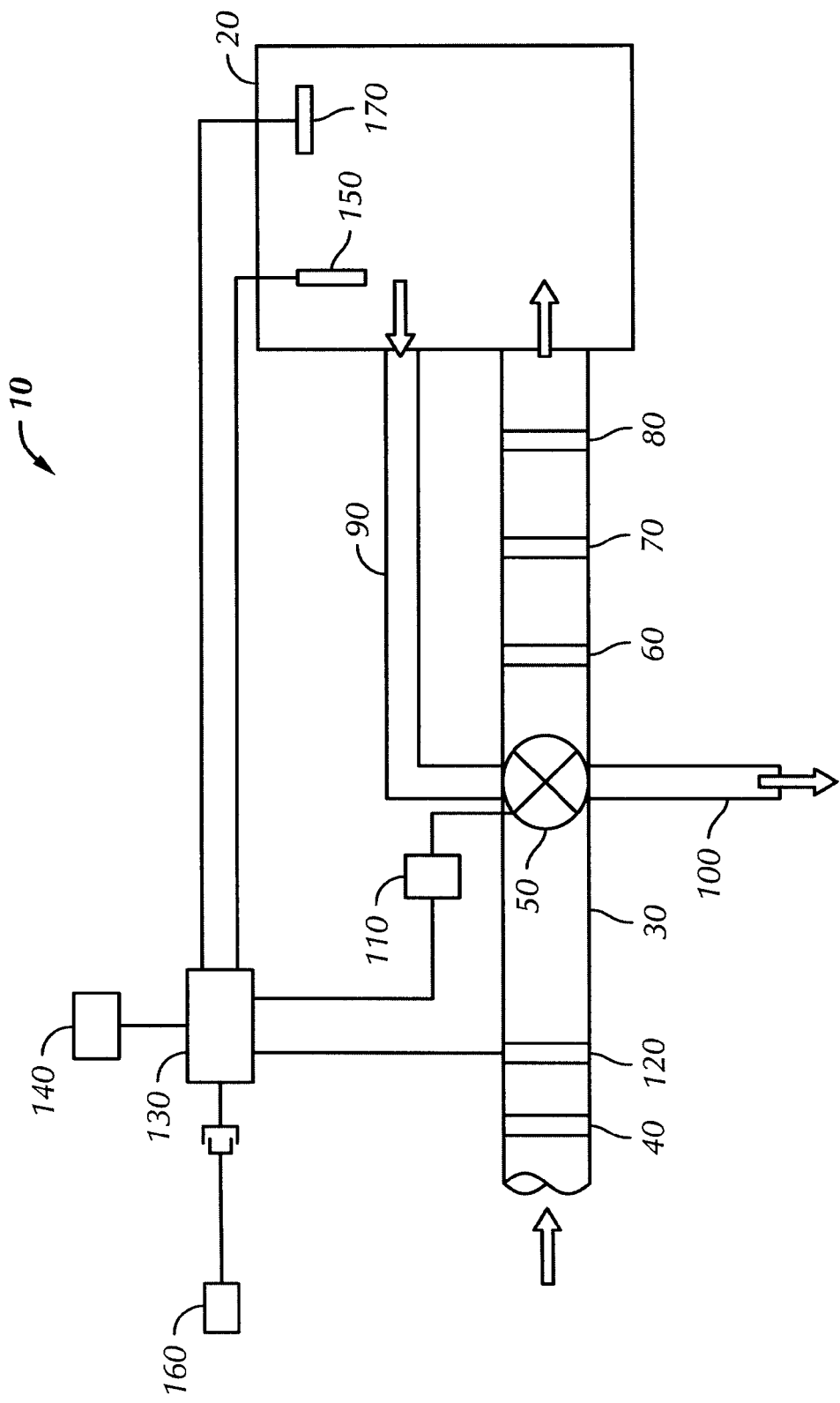
FIG. 1 is a schematic representation of a system for detection of airborne contaminants and prevention of influx of the contaminants into an enclosed space, such as a vehicle cabin, in accordance with a first presently preferred embodiment of the invention.

As used herein, when introducing elements of the present invention or the preferred embodiments thereof, the articles "a", "an", "the" and "said" are intended to mean that there are one or more of the elements. Throughout the drawings, the same reference numerals or letters are used to designate like or equivalent elements. Detailed descriptions of known functions and constructions unnecessarily obscuring the subject matter of the present invention have been omitted for clarity. The drawings are not necessarily drawn to scale.

Figure 2A:
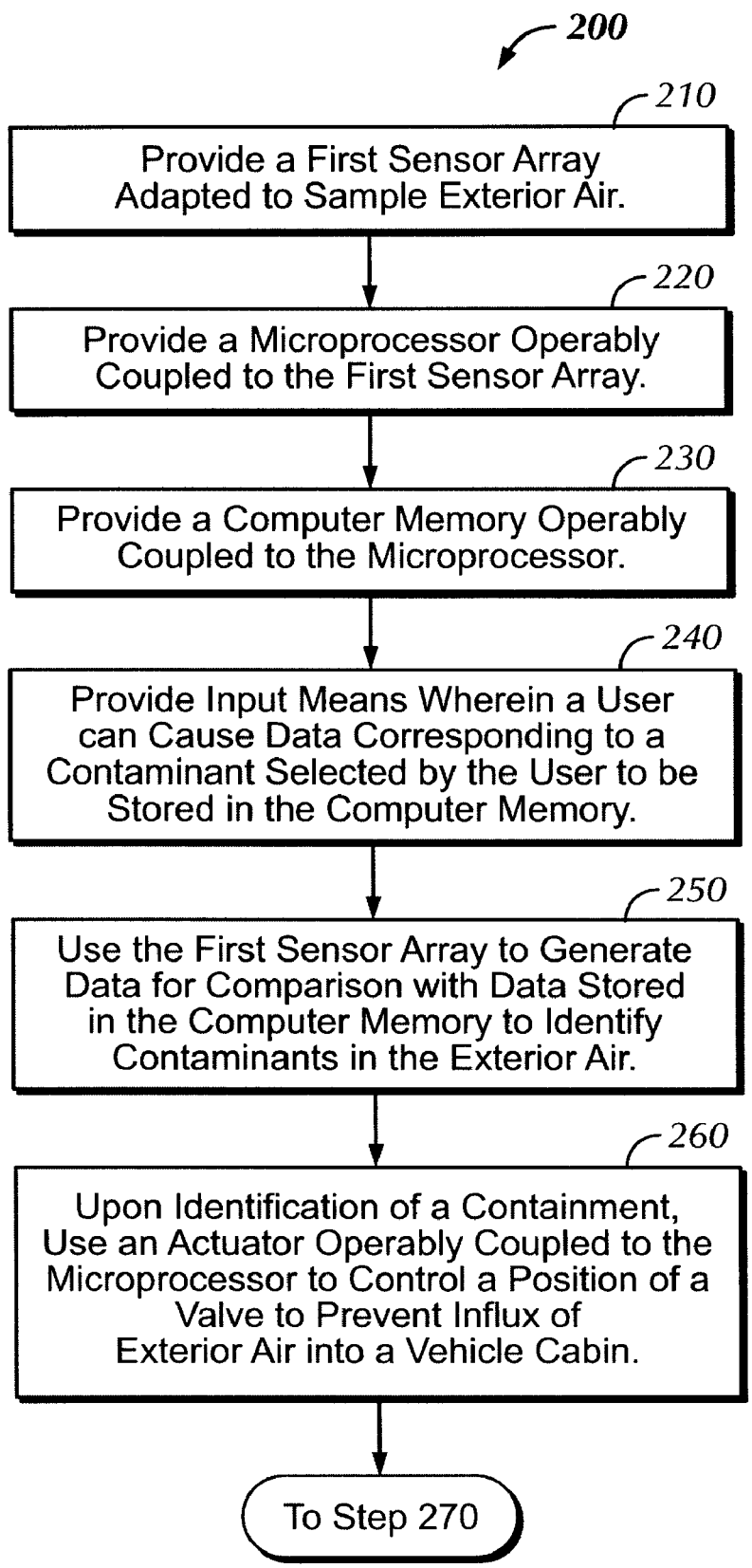
FIGS. 2A and 2B are a diagram of steps of a method of detection of airborne contaminants and prevention of influx of the contaminants into an enclosed space, such as a vehicle cabin, in accordance with a second presently preferred embodiment of the invention.
Figure 2B:
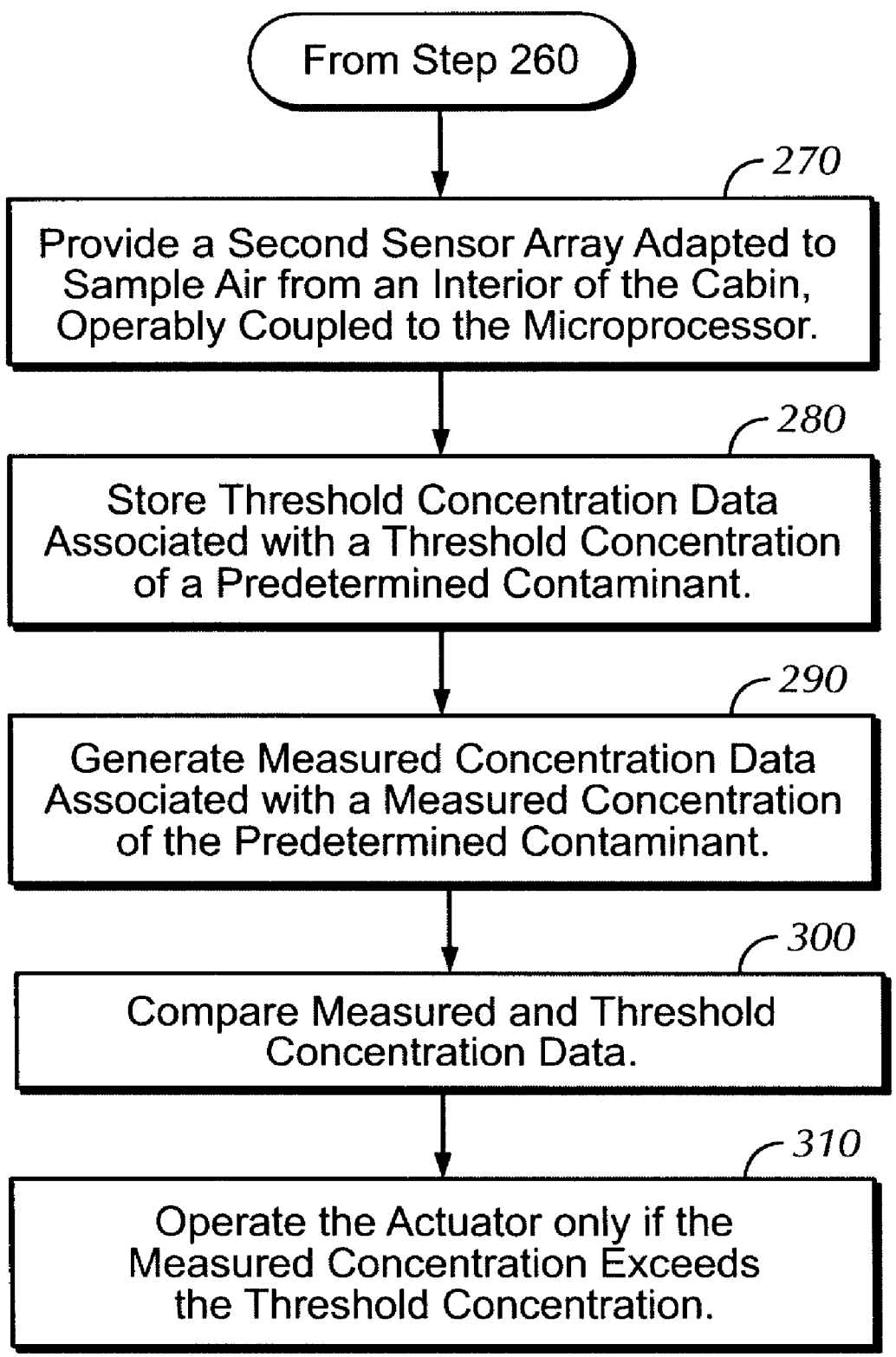

Referring to FIGS. 1, 2A, and 2B, there are shown a presently preferred embodiment of a system, generally designated 10, and a method, generally designated 200, in accordance with the present invention.

With particular reference to FIG. 1, the system 10 for detection of airborne contaminants and prevention of influx of the contaminants into an enclosed space, such as a vehicle cabin 20, is shown schematically. The vehicle cabin 20 is provided with a ventilation system. The ventilation system includes an inlet duct 30, a filter 40, a valve 50, a blower 60, a heater core 70, an evaporator core 80, a recirculation duct 90, and an exhaust duct 100. The valve 50 is capable of being moved by a valve actuator 110 between a first position wherein all of the air delivered to the vehicle cabin 20 is fresh, exterior air and a second position wherein all of the air delivered to the vehicle cabin 20 is re-circulated air, supplied to the valve 50 from the vehicle cabin 20 via the recirculation duct 90. The valve 50 may be positioned at points intermediate the first and second positions. The contaminant may create an unpleasant odor, or which poses a health risk.

The system 10 further comprises a first sensor array 120 adapted to sample exterior air prior to influx of the exterior air into the vehicle cabin 20. The first sensor array 120 is capable of generating data uniquely corresponding to each contaminant. The first sensor array 120 is of a type such as that disclosed in U.S. Pat. No. 6,495,892 (Goodman et al.). As discussed above, the '892 patent discloses a sensor array preferably formed on a single integrated circuit from conducting polymers which exhibit changes in their electrical properties when exposed to different analytes. The sensor array of the '892 patent produces a "fingerprint" uniquely associated with each analyte. Pattern recognition processing may be used to identify analytes based on the "fingerprint" data.

A microprocessor 130 is operably coupled to the first sensor array 120. A stream of data is continuously fed from the first sensor array 120 to the microprocessor 130. A computer memory 140 is operably coupled to the microprocessor 130. Data (associated with unique "fingerprints") corresponding to one or more predetermined contaminants is stored in the computer memory 140.

Input means are provided allowing a user to store in the computer memory 140 data corresponding to a contaminant selected by the user. That is, if a given contaminant is not included among the one or more predetermined contaminants, and thus the system 10 is not responsive to that given contaminant, then the user can store the "fingerprint" data associated with that given contaminant in the computer memory 140, such that upon the next occasion when the given contaminant is encountered, the system 10 will recognize it, and respond automatically. Preferably, the input means includes a switch 150, located in the vehicle cabin 20, which is accessible to a driver located in the vehicle cabin 20. Further preferably, upon selection of a contaminant by the user, the valve 50 is positioned to prevent further influx of the contaminant into the vehicle cabin 20.

The input means may further include a portable sensor array 160 capable of being operably connected and disconnected from the system 10. The portable sensor array 160 is a self-contained unit operative to: generate data to identify airborne contaminants; store the data; and, with the portable sensor array 160 operably connected to the system, download the data to the computer memory 140. Thus, for example, a user could detach the portable sensor array 160 from the system 10, and gather contaminant fingerprint data at locations within or away from the enclosed space (like the vehicle cabin 20), and then, with the portable sensor array 160 operably connected to the system 10, download the remotely-gathered contaminant fingerprint data into the computer memory 140.

The system 10 may further include deletion means operable to allow a user to delete from the computer memory 140 data corresponding to one or more of the contaminants selected by the user. The switch 150 could be provided with multiple operational positions, allowing the switch 150 to perform both the input function discussed above as well as the deletion function.

The valve actuator 110 is operably coupled to the microprocessor 130. Preferably, the valve actuator 110 is very fast responding, to reduce the amount of time between when a contaminant is identified by the microprocessor 130 and when the valve 50 is moved to a desired position.

Preferably, the first sensor array 120 is positioned outside of the vehicle cabin 20 and is more preferably positioned in the inlet duct 30 just downstream of the filter 40. Positioning the first sensor array 120 downstream of the filter 40 reduces the amount of dirt deposited on the first sensor array 120, and thus reduces maintenance requirements.

Further preferably, the volume of the inlet duct 30; the volume flowrate through the inlet duct 30 (which is defined by the operating characteristics of the blower 60); and the response characteristics of the first sensor array 120, the microprocessor 130, the valve actuator 110, and valve 50 are selected to allow the valve 50 to be positioned to prevent influx of exterior air in a short period of time following identification of a contaminant in the exterior air. Ideally, the system 10 response characteristics are such that valve 50 is closed prior to influx of a contaminant into the vehicle cabin 20 upon identification of the contaminant based on data stored in the computer memory 140.

In operation, exterior air moves through the inlet duct 30 under action of the blower 60. The exterior air passes through the filter 40, and then passes over the first sensor array 120. The first sensor array 120 generates data for comparison with data stored in the computer memory 140 to identify contaminants in the exterior air. If the data ("fingerprint") matches data already stored in the computer memory 140, and if the valve 50 is positioned such that exterior air is being admitted into the vehicle cabin 20, thus indicating that an undesired contaminant is about to enter the vehicle cabin 20, then the microprocessor 130 operates the valve actuator 110 to control the position of the valve 50 to prevent influx of the exterior air into the vehicle cabin 20.

Optionally and preferably, the system 10 further comprises a second sensor array 170 adapted to sample air from an interior of the vehicle cabin 20. The second sensor array 170 is operably coupled to the microprocessor 130. The microprocessor 130 controls the actuator to position the valve 50 to admit exterior air into the cabin 20 upon identification by the microprocessor 130 of a contaminant within the cabin 20 having data stored in the computer memory 140. The second sensor array 170 is preferably similar in construction and operation to the first sensor array 120 as described above. In particular, it is desirable that the user have the ability to select contaminants sensed by the second sensor array 170 for storage in the computer memory 140, as described above relative to the first sensor array 120.

Further preferably, in a manner similar to that disclosed in U.S. Pat. No. 5,571,401 (Lewis et al.), the first sensor array is provided with the ability to discriminate between first and second concentrations of a given contaminant. That is, the computer memory 140 includes threshold concentration data associated with a threshold concentration of at least one of the one or more predetermined contaminants. The threshold concentration is predefined as a concentration at which the average occupant of the vehicle cabin 20 is not offended, disturbed, nor harmed by the contaminant. The first sensor array 120 has the capability to generate measured concentration data associated with a measured concentration of the at least one of the one or more predetermined contaminants. The microprocessor 130 operates to compare the measured concentration data with the threshold concentration data and further operates the actuator 110 only if the measured concentration exceeds the threshold concentration.

With reference now to FIGS. 2A and 2B, a method 200 for detection of airborne contaminants and prevention of influx of the contaminants into an enclosed space, such as vehicle cabin 20, is illustrated. While steps of the method 200 are identified herein as "first", "second", and so forth, it is to be understood that such nomenclature is for convenience only, and does not necessarily imply that the steps must be performed in a specific sequential order. Given that understanding, the method 200 comprises a first step 210 of providing first sensor array 120 adapted to sample exterior air prior to influx of the exterior air into the vehicle cabin 20. As discussed above herein, the first sensor array 120 is capable of generating data uniquely corresponding to each contaminant. In a second step 220, microprocessor 130, operably coupled to the first sensor array 120, is provided. In a third step 230, computer memory 140, operably coupled to the microprocessor 130 and having data stored therein corresponding to one or more predetermined contaminants, is provided. In a fourth step 240, input means (including, for example, the switch 150) are provided, wherein a user can cause data corresponding to a contaminant selected by the user to be stored in the computer memory 140. In a fifth step 250, the first sensor array 120 is used to generate data for comparison with data stored in the computer memory 140 to identify contaminants in the exterior air. Upon identification of a contaminant having data stored in the computer memory 140, in a sixth step 260, valve actuator 110, operably coupled to the microprocessor 130 to control a position of valve 50, is operated to prevent influx of exterior air into the cabin 20.

Preferably, the method 200 further comprises a seventh step 270 of providing the second sensor array 170. As discussed above, the second sensor array 170 is adapted to sample air from an interior of the cabin 20 and is operably coupled to the microprocessor 130. The microprocessor 130 controls the actuator 110 to position the valve 50 to admit exterior air into the cabin 20 upon identification by the microprocessor 130 of a contaminant within the cabin 20.

Further preferably, the method 200 further comprises an eighth step 280 of storing threshold concentration data associated with a threshold concentration of at least one predetermined contaminant in the computer memory 140. In a ninth step 290, the first sensor array 120 generates measured concentration data associated a measured concentration of the at least one of the one or more predetermined contaminants. In a tenth step 300, the measured concentration data is compared with the threshold concentration data. In an eleventh step 310, the actuator 110 is operated to control a position of the valve 50 only if the measured concentration exceeds the threshold concentration.

From the foregoing it can be seen that the present invention provides a system and method for detecting airborne contaminants and preventing influx of the contaminants into an enclosed space, such as a vehicle cabin. The system and method allow a user to select or "flag" contaminants and store "fingerprint" data associated with the selected contaminants in computer memory 140.

It will be appreciated by those skilled in the art that changes could be made to the embodiments described above without departing from the broad inventive concept thereof. It is to be understood, therefore, that this invention is not limited to the particular embodiments disclosed, but it is intended to cover modifications within the spirit and scope of the present invention as defined by the appended claims.

That which is claimed is:

1. A system for detection of airborne contaminants and prevention of influx of the contaminants into a vehicle cabin, the vehicle cabin being provided with a ventilation system including at least one valve, the system comprising:
    a first sensor array adapted to sample exterior air prior to influx of the exterior air into the cabin, wherein the first sensor array is installed in an air inlet duct of the ventilation system and is capable of generating data uniquely corresponding to each contaminant;
    a microprocessor operably coupled to the first sensor array;
    a computer memory operably coupled to the microprocessor and having data stored therein corresponding to one or more predetermined contaminants;
    input means wherein a user can cause data corresponding to a contaminant selected by the user to be stored in the computer memory; and
    an actuator operably coupled to the microprocessor, wherein:
        the first sensor array generates data for comparison with data stored in the computer memory to identify contaminants in the exterior air; and
        the actuator is operative to control a position of the at least one valve to prevent influx of the exterior air into the cabin upon identification of a contaminant having data stored in the computer memory; and
        the input means includes a portable sensor array capable of being operably connected to and disconnected from the system, wherein the portable sensor array is a self-contained unit operative to: generate data to identify airborne contaminants; store the data; and, with the portable sensor array operably connected to the system, download the data to the computer memory.

2. The system of claim 1, wherein the contaminant creates an unpleasant odor.

3. The system of claim 1, wherein the contaminant poses a health risk.

4. The system of claim 1, wherein the first sensor array is formed on a single integrated circuit.

5. The system of claim 1, wherein the first sensor array comprises conducting polymers exhibiting changes in electrical properties upon exposure to the contaminants.

6. The system of claim 1, wherein the first sensor array is positioned outside of the cabin.

7. The system of claim 1, wherein a volume of the air inlet duct, a maximum volume flowrate through the air inlet duct, and response characteristics of the first sensor array, microprocessor, actuator, and valve are selected to allow the valve to be positioned to prevent influx of exterior air prior to influx of the contaminate into the cabin upon identification of the contaminate having data stored in the computer memory.

8. The system of claim 1, further comprising a second sensor array adapted to sample air from an interior of the cabin and operably coupled to the microprocessor, wherein the microprocessor controls the actuator to position the valve to admit exterior air into the cabin upon identification by the microprocessor of a contaminant within the cabin having data stored in the computer memory.

9. The system of claim 1, wherein the input means includes a switch accessible to a driver from the vehicle cabin.

10. The system of claim 1 further comprising deletion means operable to allow a user to delete from the computer memory data corresponding to one or more of the contaminants previously selected by the user.

11. The system of claim 1, wherein the valve is positioned to prevent influx of exterior air into the cabin upon selection by the user of the contaminant.

12. The system of claim 1, wherein the computer memory includes threshold concentration data associated with a threshold concentration of at least one of the one or more predetermined contaminants.

13. The system of claim 12, wherein the first sensor array generates measured concentration data associated with a measured concentration of the at least one of the one or more predetermined contaminants.

14. The system of claim 13, wherein the microprocessor is operative to compare the measured concentration data with the threshold concentration data and is further operative to operate the actuator only if the measured concentration exceeds the threshold concentration.

* * * * *